United States Patent [19]

Irwin

[11] 4,282,210
[45] Aug. 4, 1981

[54] METHOD FOR THE CONTROL OF SHIPPING FEVER PNEUMONIA IN CATTLE

[75] Inventor: Michael R. Irwin, New City, N.Y.

[73] Assignee: American Cyanamid Co., Stamford, Conn.

[21] Appl. No.: 105,687

[22] Filed: Dec. 20, 1979

[51] Int. Cl.³ .............................................. A61K 39/12
[52] U.S. Cl. ...................................... 424/89; 424/270
[58] Field of Search ................................. 424/89, 270

[56] References Cited

U.S. PATENT DOCUMENTS 3,907,986  9/1975  Zygraich .............................. 424/89

OTHER PUBLICATIONS

Renoux–Chem. Abst., vol. 79, (1973), p. 135,189v.
Texas Agricul. Exper. Sta. Research News Report 78-13, Aug. 10, 1978, pp. 1–3.

*Primary Examiner*—Sam Rosen
*Attorney, Agent, or Firm*—H. G. Jackson

[57] ABSTRACT

There is provided a method for the control of shipping fever pneumonia in cattle, comprising administering to said cattle an immunizing amount of an infectious bovine rhinotracheitis virus vaccine and a potentiating amount of a potentiator therefor, selected from the group consisting of pharmaceutically acceptable salts of dl 6-phenyl-2,3,5,6-tetrahydroimidazo[2,1-b]thiazole and pharmaceutically acceptable salts of 1(−)6-phenyl-2,3,5,6-tetrahydroimidazo[2,1-b]thiazole. This invention also relates to a method for reducing morbidity associated with shipping fever pneumonia in cattle by the parenteral treatment of said cattle with from 2 mg/kg to 8 mg/kg of animal body weight of a pharmaceutically acceptable salt of dl 6-phenyl-2,3,5,6-tetrahydroimidazo[2,1-b]thiazole or 1(−)6-phenyl-2,3,5,6-tetrahydroimidazo[2,1-b]thiazole and a prophylactically effective amount of infectious bovine rhinotracheitis virus vaccine.

5 Claims, 3 Drawing Figures

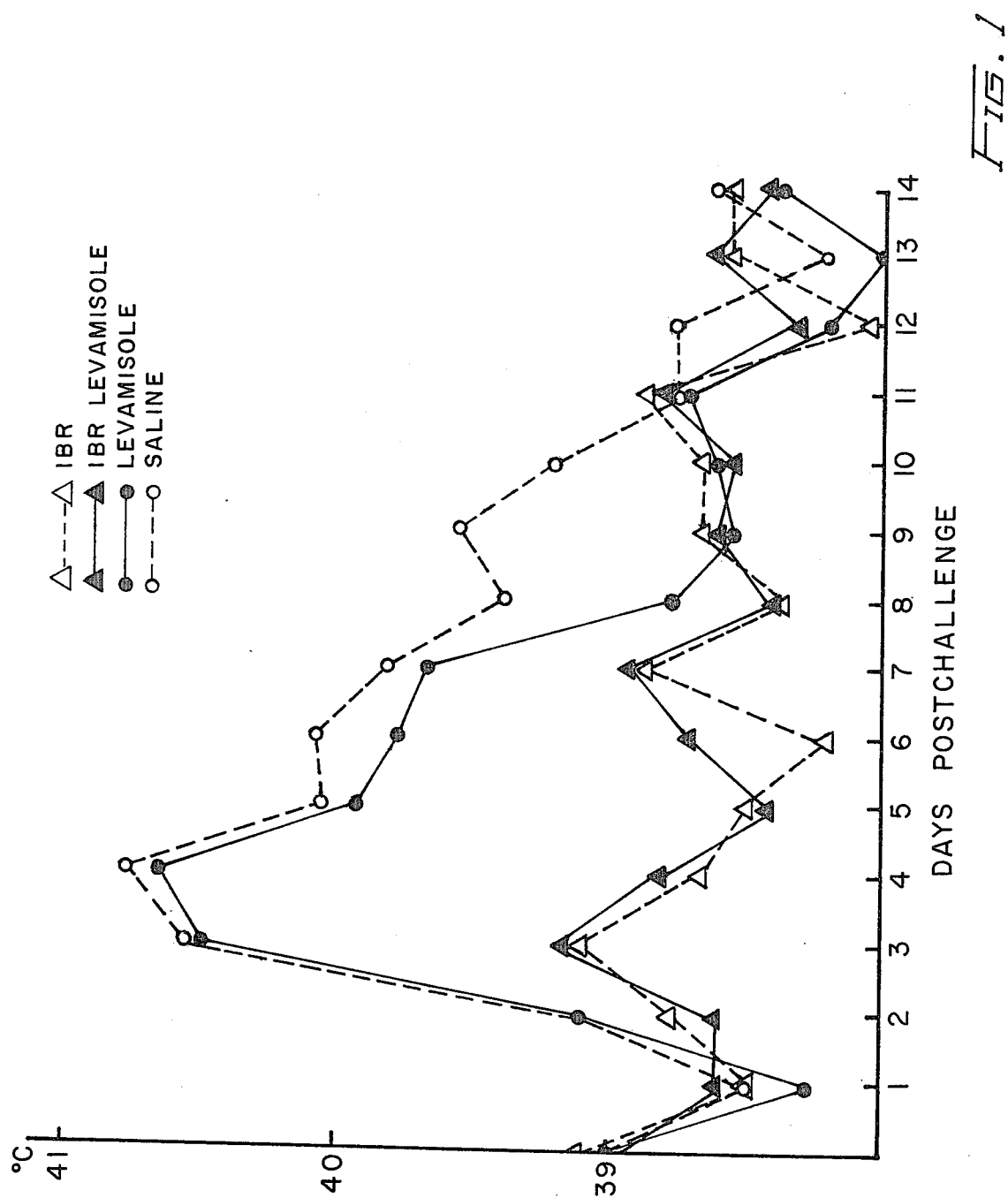

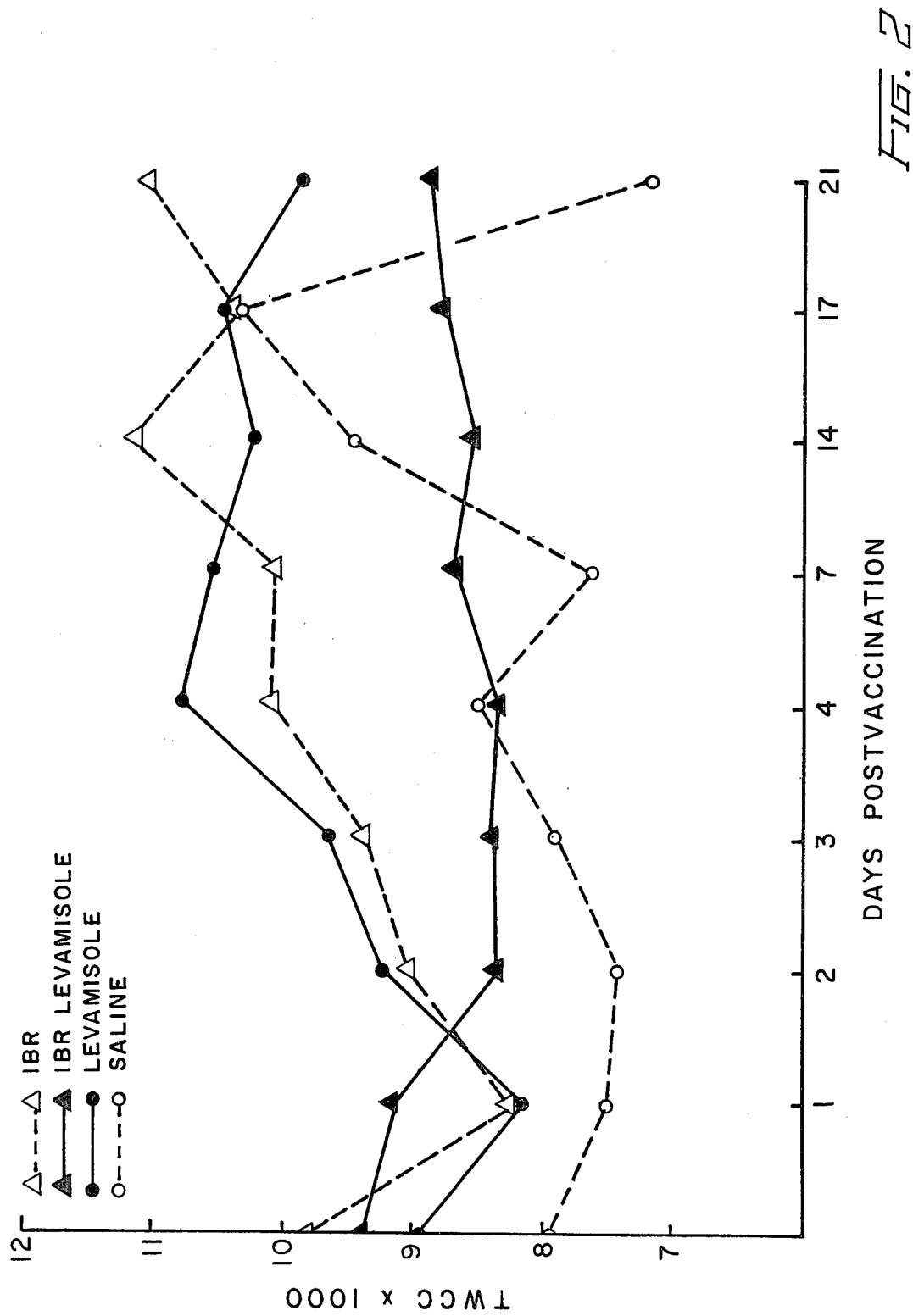

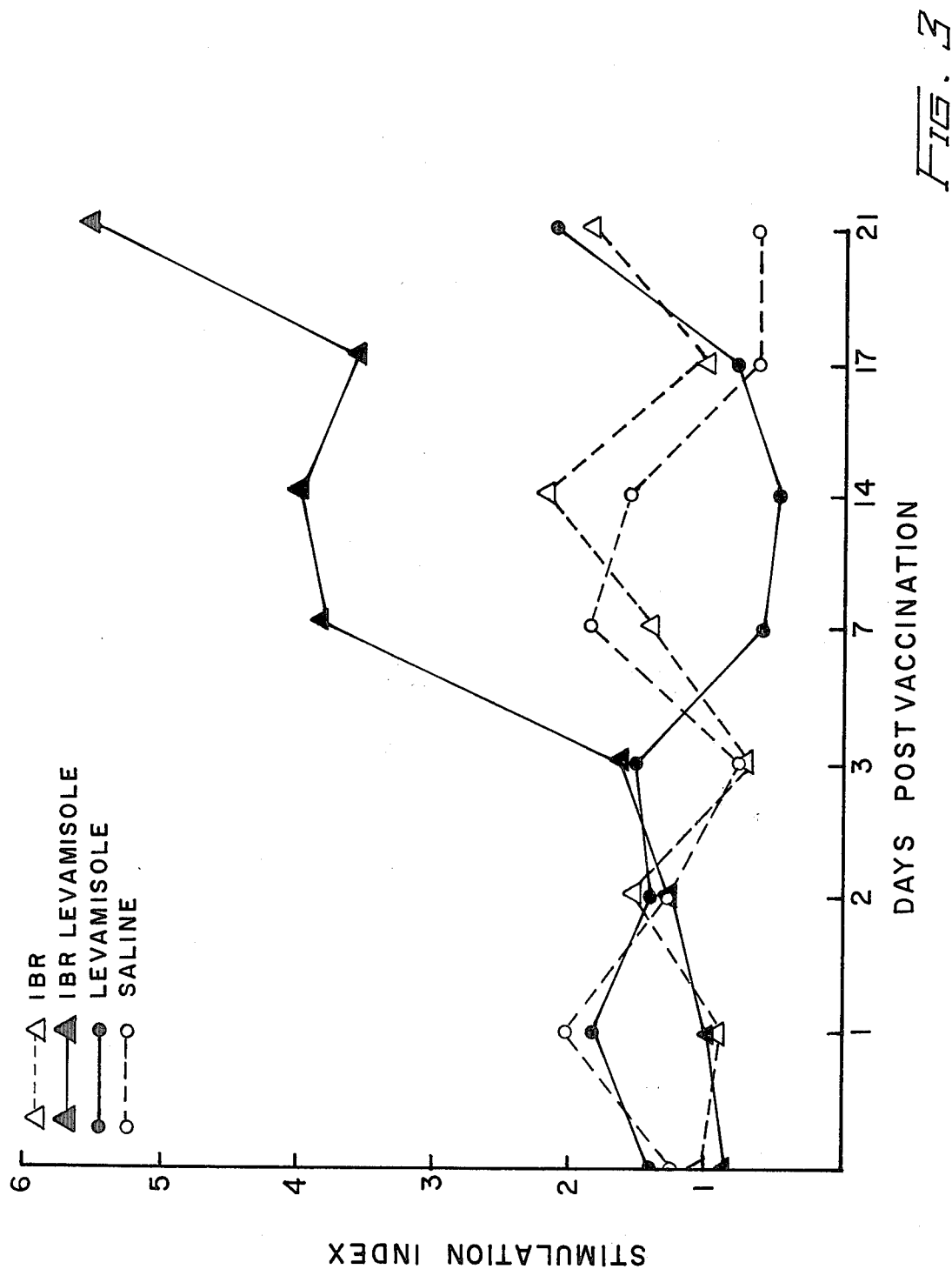

METHOD FOR THE CONTROL OF SHIPPING FEVER PNEUMONIA IN CATTLE

SUMMARY OF THE INVENTION

Shipping fever is generally recognized, by those involved in the beef cattle industry, as the disease responsible for a major portion of the economic losses encountered in the production and handling of cattle. The syndrome is characterized clinically by fever, acute inflammation of the airways, nasal discharge, anorexia, depression, fibrimous pneumonia, necrosis of the tissues involved, and is a major cause of death among young cattle. The disease is most frequently encountered in feedlots following shipping and is responsible for an estimated annual loss to the industry of one hundred million dollars. This loss is directly attributable to mortality associated with the disease, the high costs of prophylaxis and treatment, the loss of weight and condition, and incomplete recovery from the disease which results in poorer weight gains.

The pathogenesis of shipping fever is generally considered to involve adverse external influences predisposing to the initiation of a viral respiratory infection which, in turn, produces a pabulum favorable for the proliferation of bacteria. Previous research has concentrated on the prevention of the disease by vaccine development, changes in management procedures, and antibiotic therapy. Some improvements in these areas have been made as a result of this research, however, no entirely satisfactory method for inhibiting and/or treating shipping in cattle has, heretofore, been disclosed.

It is therefore an object of this invention to provide a method for the prophylactic treatment of cattle subject to stress, viral infection and/or bacterial infection, to inhibit and/or prevent the development of shipping fever in said cattle.

It is also an object of this invention to provide a method for treating cattle exhibiting clinical signs of shipping fever to reduce the debilitating effects of said disease on said cattle.

In accordance with this invention, I have found that shipping fever can be controlled in cattle by parenterally administering to said cattle from about 2 mg/kg of body weight to 8 mg/kg of body weight, and preferably 6 to 8 mg/kg of body weight, of a pharmacentically acceptable salt, preferably the phosphate salt, of a compound selected from the group consisting of dl 6-phenyl-2,3,5,6-tetrahydroimidazo[2,1-b]thiazole and 1(−)6-phenyl-2,3,5,6-tetrahydroimidazo[2,1-b]thiazole and an immunizing or prophylactically effective amount of an infectious bovine rhinotracheitis virus vaccine.

In practice I have found that the above-mentioned drugs are highly effective for inhibiting or reducing shipping fever in stressed cattle when they are parenterally administered to said cattle essentially simultaneously, i.e. on the same day. I have also found that the treatment of cattle with the above-mentioned drugs is highly effective for controlling shipping fever in cattle when the dl or 1(−)6-phenyl-2,3,5,6-tetrahydroimidazo[2,1-b]thiazole salt is parenterally administered to said cattle prior (from 1 to 21 days) to parenteral administration of the infectious bovine rhinotracheitis (IBR) virus vaccine. The latter treatment, as well as the simultaneous administration of said drugs, results in the potentiation of the activity of the IBR vaccine by the parenterally administered thiazole salt. This is evidenced by the fact that in animals receiving the above-treatments, nasal shedding of the virus following challenge with a viralent strain of infectious bovine rhinotracheitis vaccine occurs over a much shorter period than it does in animals receiving only the IBR vaccine or the thiazole salt. It has also been observed that morbidity in cattle treated in accordance with the method of the present invention is significantly less than it is in animals treated with the IBR vaccine alone or in animals treated with the IBR vaccine and an orally administered pharmaceutically acceptable salt of 1(−)6-phenyl-2,3,5,6-tetrahydroimidazo[2,1-b]thiazole.

Surprisingly, it is also noted that when the order of administration of the drugs is reversed, there is no apparent potentiation of the IBR vaccine by the abovesaid thiazole salt.

The treatment method of the present invention thus requires parenteral administration of from 2 to 8 mg/kg of bodyweight of the pharmaceutically acceptable salt of dl or 1(−)6-phenyl-2,3,5,6-tetrahydroimidazo[2,1-b]thiazole, the same day or from 1 to 21 days prior to vaccination of said cattle with an immunizing or prophylactically effective amount (usually 1 to 2 ml parenterally administered) of an infectious bovine rhinotracheitis virus vaccine. For effective vaccination the IBR vaccine should provide about 16,000 to 3,163,000 tissue culture infective dose (TCID$_{50}$'s).

EXAMPLE 1

Evaluation of parenterally administered 1(−)6-phenyl-2,3,5,6-tetrahydroimidazo[2,1-b]thiazole phosphate as a potentiator for parenterally administered infectious bovine rhinotracheitis virus vaccine In this evaluation, conventionally raised, IBR-seronegative, mixed breed feeder calves (12 heifers and 9 steers) weighing approximately 162 kg each were confined in open lots and given ad libitum feed (high energy concentrate and roughage) and water. The calves which were previously found to have a low worm burden were alloted to 4 groups on arrival at the feedlot. Two groups of calves each were given 1(−)6-phenyl-2,3,5,6-tetrahydroimidazo[2,1-b]thiazole phosphate, i.e. levamisole PO$_4$, (by subcutaneous injection) at a dosage rate of 6 mg/kg body weight or a similar volume of sterile normal saline by the same route. The other two groups of 5 and 6 calves each were similarly given either saline or levamisole by subcutaneous injection at the same time as a commercially prepared infectious bovine rhinotracheitis (IBR) viral vaccine with an aqueous leptospirosis diluent. The calves in the 2 groups receiving the IBR vaccine were confined in a pen with handling facilities, which were completely isolated from the pen and handling facilities used for the other 2 non-vaccinated groups. All the calves were challenged intranasally in the form of a spray 14 days after initiation of the experiment with a tissue culture infective dose (TCID) 1 ml ($5 \times 10^6$ TCID 50/ml) of the Cooper Strain of IBR virus (VB-APHIS-USDA; lot # IBR 74-1).

Virus isolation attempts were made from nasal samples obtained from every calf before and on each of 14 days following challenge. These specimens were obtained by nasal swabbings made by inserting and rotating cotton tipped wood applicator sticks into each nostril. The swabs were then placed in 2 ml of Eagle's minimum essential madium (MEM) containing 0.11% NaHCO$_3$, 1,000 μg of pencillin, 1,000 μg of streptomycin and 250 μg of fungizone per ml of media. Within 4 hours of sampling, the fluid was extracted from each swab and centrifuged at 1,500×g for 10 min. Viral isolation attempts were made using 0.2 ml of supernatent fluid in each of 4 tubes of mycoplasma free Madin Darby bovine kidney (MDBK) cell cultures. The specimen was considered to have been free of virus at the time of collection if no cytopathogenic effects (CPE) was observed in the 4 tubes during the 7 days following innoculation.

The viral isolates were identified by a commercially prepared fluorescein-conjugated rabbit anti-IBR serum. Infected monolayers of MDBK cells grown on coverslips in Leighton tubes were washed once with a phosphate buffered saline solution (pH 7.2 containing 0.001 M phosphate) rinsed in deionized water, air dried and fixed in acetone for 10 minutes. Following staining and mounting, cell monolayers were observed for fluorescence by a dark-field ultraviolet microscopy using a microscope equipped with a mercury arc lamb for illumination.

For the lymphocyte transformation studies the IBR virus (Colorado strain) was propogated on MDBK cells. The tissue culture fluids (600 ml) were harvested and centrifuged at 1,000×g for 10 minutes. The supernatent fluids with a virus titre of $10^{6.7}$ TCID 50/ml were further centrifuged at 40,000×g at 4 C for 1 hr. The virus pellet was resuspended in 6 ml of RPMI 1640 medium and later diluted 100 X in the same medium. The IBR containing fluid was inactivated by exposure to ultra violet radiation. On ml aliquot of infected fluid was placed in 35 mm plastic petri dishes and irradiated for 30 minutes by an ultraviolet source at a distance of 11 cm. After irradiation the fluids were stored at −80 C. while an aliquot was examined for residual live virus—which was found. The infective fluid was therefore exposed to a further 15 minutes of ultraviolet radiation. The final preparation was stored in 1 ml aliquots at −80 C.

Lymphocyte preparations for in vitro stimulations were prepared by the following procedure: A 2 ml sample of blood collected by jugular venipuncture in heparin coated tubes, was diluted with 4 ml of RPMI 1640 medium, gently layered onto a density gradient of 4.8 ml of 9% ficoll together with 2 ml of 33.75% diatrizoate and centrifuged at 1,200×g in a round bottomed tube (17×100 mm) for 30 minutes at room temperature. The lymphocyte rich band above the ficoll—diatrizoate mixture was removed and washed once in RPMI 1640 medium at 400×g for 6 minutes, after which the cells were suspended for mechanical counting[a] and cell concentrations adjusted with growth media (RPMI 1640 with 15% Fetal calf serum, 60 μg/dl of L glutamine, 100μ of penecillin and 100 μg streptomycin/ml) to 1×10⁶ cells/ml. Triplicate 0.2 ml samples of diluted lymphocytes were placed in flat bottomed wells of microtitre plates and mixed with 0.02 ml of either Concanavalin A (lot #16C-7090 diluted 50 μg/ml in RPMI 1640 medium), Pokeweed mitogen[d] (lot #A-771101, diluted 1:4 in distilled $H_2O$), IBR antigen (diluted 1:8 in RPMI 1640 medium), or in the control cultures RPMI 1640 medium alone. Lymphocyte cultures were incubated for 48 hours at 37 C in a humidified 5% $CO_2$ atmosphere, after which 0.05 ml of a diluted tritiated thymidine solution[c] (methyl-³H thymidine specific activity 6.7 Ci/mmol) was added to all cultures and incubated for an additional 24 hours. The cells were mechanically harvested[a] on filter paper strips[b]. Appropriate pieces of paper were placed in microscintillation tubes[c] containing 3 ml of scintillation fluid. Samples were counted for 5 minutes in a soft-beta spectrophotometer[d]. The stimulation index was calculated by dividing the mean counts per minutes obtained in the stimulated cultures by the mean counts per minutes obtained in controlled unstimulated cultures.

The stimulation indices and TWC counts were compared using Students't test. The morbidity and mortality in the different groups were compared using the normal test proportions.

From this experiment it can be seen that rectal temperatures of all the cattle remined within the normal limits until after challenge, when the unvaccinated animals experience a fever which reached a mean maximum of 40.75 C, 4 days post challenge (FIG. 1). The cattle treated with levamisole alone tended to recover more rapidly than those treated with saline as their mean temperature returned to levels observed in the vaccinated calves, 8 days after challenge while the temperatures of the cattle receiving saline alone returned to the same level 11 days after challenge.

The mean total white cell (TWC) count of the cattle vaccinated and treated with levamisole was lower during days 2 to 21 post vaccination than the mean counts of the cattle given vaccine alone (FIG. 2). The opposite was observed in the cattle treated with levamisole alone in that the mean TWC count was higher than the mean count of the cattle receiving saline alone. These differences were most noticeable during the first 7 days post treatment and on day 21 ($P<0.01$) (FIG. 2).

The nasal shedding of virus following challenge with a virulent strain of IBR was used to evaluate the effect of levamisole treatment on the ability of calves to resist or recover from an IBR infection. The calves receiving levamisole with or without IBR vaccination shed the virus for a shorter period of time (6.6 and 10.2 days respectively), compared to the groups receiving saline with or without IBR vaccination (7.4 and 10.8 days respectively). The most noticeable difference was observed in the group receiving levamisole at the time of vaccination (Table I).

The mean in vitro stimulation index (SI), which was used to determine the specific lymphocyte response to an IBR antigen, remained within the approximate pretreatment levels in all the groups other than the group receiving levamisole at the time of vaccination (FIG. 3). This latter group, when compared with the pretreatment level had a 4 fold increase in the SI on days 7,14 and 17 and an approximate 6 fold ($P<0.1$) increase on day 21.

The effect of levamisole treatment on the SI associated with the in vitro lymphocyte response to nonspecific mitrogens is presented in Table II. The SI of the calves' lymohocytes response to Con A and PWM after challenge tended to be higher in the non-vaccinated group receiving saline than the comparable group treated with levamisole, while in the IBR vaccinated groups on days 17 and 21, the SI of calves treated with levamisole were higher than those given saline.

TABLE I

The virus shedding rate and mean duration of shedding of IBR following challenge in vaccinated or non vaccinated calves treated with either levamisole or saline

| Treatment | \[0\][a] | 1[a] | 2 | 3 | 4 | 5 | 6 | 7 | 8 | 9 | 10 | 11 | 12 | 13 | 14 | Mean Duration of Virus Shedding (days) |
|---|---|---|---|---|---|---|---|---|---|---|---|---|---|---|---|---|
| IBR vaccination & levamisole (n = 6) | 0 | 100 | 100 | 100 | 83 | 66 | 66 | 50 | 50 | 33 | 16 | 0 | 0 | 0 | 0 | 6.6 |
| IBR vaccination & saline (n = 5) | 0 | 100 | 100 | 100 | 100 | 100 | 100 | 60 | 40 | 20 | 20 | 20 | 0 | 0 | 0 | 7.4 |
| Levamisole (n = 5) | 0 | 100 | 100 | 100 | 100 | 100 | 100 | 100 | 100 | 80 | 80 | 40 | 20 | 0 | 0 | 10.2 |
| Saline (n = 5) | 0 | 100 | 100 | 100 | 100 | 100 | 100 | 100 | 100 | 100 | 100 | 60 | 20 | 0 | 0 | 10.8 |

[a] = Days post challenge

TABLE II

Concanavalin A (Con A) and Pokeweed mitogen (PWM) stimulation of lymphocytes of vaccinated or non vaccinated calves treated with either levamisole $PO_4$ or saline

| | Principles (given levamisole $PO_4$) | | | | Controls (given saline solution) | | | |
|---|---|---|---|---|---|---|---|---|
| | Vaccinated with IBR (n = 6) | | Non Vaccinated (n = 5) | | Vaccinated with IBR (n = 5) | | Non Vaccinated (n = 5) | |
| Days after Treatment | Con A SI | PWM SI | Con A SI | PWM SI | Con A SI | PWM SI | Con A SI | PWM Si |
| 0 | 158.4 | 101.5 | 168.4 | 85.4 | 153.8 | 116.6 | 277.8 | 181.6 |
| 1 | 125.3 | 81.5 | 186.4 | 119.7 | 215.0 | 106.2 | 409.9 | 271.4 |
| 2 | 252.6 | 170.6 | 322.4 | 157.9 | 284.8 | 149.5 | 440.9 | 271.4 |
| 3 | 332.2 | 210.3 | 284.8 | 188.8 | 259.0 | 171.8 | 327.7 | 207.0 |
| 7 | 101.5 | 89.1 | 50.0 | 41.3 | 52.3 | 51.0 | 311.8 | 70.6 |
| 14 | 127.3 | 107.2 | 49.0 | 39.2 | 100.6 | 81.2 | 161.6 | 113.9 |
| 17 | 134.8 | 105.8 | 80.6 | 53.9 | 57.1 | 44.8 | 159.8 | 105.9 |
| 21 | 126.8 | 92.6 | 38.2 | 29.3 | 68.0 | 53.4 | 79.0 | 60.6 |

Con A = Concanavalin A
PWM = Pokeweed Mitogen
= Stimulation Index

I claim:

1. A method for the control of shipping fever in cattle comprising parenterally administering to said animals from 2 mg/kg of body weight to 8 mg/kg of body weight of a pharmaceutically acceptable salt of a compound selected from the group consisting of dl 6-phenyl-2,3,5,6-tetrahydroimidazo-[2,1-b]thiazole and 1(—)6-phenyl-2,3,5,6-tetrahydroimidazo-[2,1-b]thiazole and, the same day or within 21 days thereafter, parenterally administering to said cattle an immunizing or prophylactically effective amount of an infectious bovine rhinotracheitis virus vaccine.

2. A method according to claim 1 wherein the infectious bovine rhinotracheitis virus vaccine is administered at a dose level which provides said treated animals with from 16,000 to 3,163,000 tissue culture infective dose ($TCID_{50}$'s).

3. A method according to claim 2 wherein the thiazole salt employed in said treatment is 1(—)6-phenyl-2,3,5,6-tetrahydroimidazo-[2,1-b]thiazole phosphate and is administered to said animals at the dose level of 6 mg/kg of animal body weight.

4. A method for potentiating the activity of infectious bovine rhinotracheitis vaccine to control shipping fever in cattle comprising administering parenterally from 16,000 to 3,163,000 $TCID_{50}$'s of said vaccine and subsequently, parenterally administering to said cattle from 2 mg/kg of body weight to 8 mg/kg of body weight of a pharmaceutically acceptable salt of dl 6-phenyl-2,3,5,6-tetrahydroimidazo[2,1-b]thiazole or 1(—)6-phenyl-2,3,5,6-tetrahydroimidazo[2,1-b]thiazole.

5. A method according to claim 4 wherein said thiazole is 1(—)6-phenyl-2,3,5,6-tetrahydroimidazo[2,1-b]thiazole phosphate and is parenterally administered at a dose level of 6 mg/kg of animal body on the same day the infectious bovine rhinotracheitis virus vaccine is administered to said cattle.

* * * * *